United States Patent
Goel et al.

(10) Patent No.: US 9,522,068 B2
(45) Date of Patent: Dec. 20, 2016

(54) MINIMALLY INVASIVE COLLAPSIBLE CAGE

(75) Inventors: Vijay K. Goel, Holland, OH (US); Aaron Matyas, Maumee, OH (US)

(73) Assignee: THE UNIVERSITY OF TOLEDO, Toledo, OH (US)

( * ) Notice: Subject to any disclaimer, the term of this patent is extended or adjusted under 35 U.S.C. 154(b) by 0 days.

(21) Appl. No.: 13/254,965

(22) PCT Filed: Mar. 12, 2010

(86) PCT No.: PCT/US2010/027175
§ 371 (c)(1),
(2), (4) Date: Sep. 23, 2011

(87) PCT Pub. No.: WO2010/105181
PCT Pub. Date: Sep. 16, 2010

(65) Prior Publication Data
US 2012/0004732 A1    Jan. 5, 2012

Related U.S. Application Data

(60) Provisional application No. 61/160,051, filed on Mar. 13, 2009.

(51) Int. Cl.
*A61F 2/44* (2006.01)
*A61F 2/30* (2006.01)

(52) U.S. Cl.
CPC .... *A61F 2/4455* (2013.01); *A61F 2002/30507* (2013.01); *A61F 2002/30523* (2013.01);
(Continued)

(58) Field of Classification Search
CPC .................. A61F 2/4425; A61F 2002/30624;
A61F 2002/30471; A61F 2002/30484; A61F 2002/3052; A61F 2220/009; A61B 17/7065
(Continued)

(56) References Cited

U.S. PATENT DOCUMENTS 5,171,278 A    12/1992 Pisharodi
5,545,229 A    8/1996 Parsons et al.
(Continued)

FOREIGN PATENT DOCUMENTS

WO    9214423 A1    9/1992
WO    9834568 A1    8/1998
(Continued)

OTHER PUBLICATIONS

International Search Report, Application No. PCT/US2010/27175 dated May 11, 2010.
(Continued)

*Primary Examiner* — Jan Christopher Merene
*Assistant Examiner* — Atiya Mahmud
(74) *Attorney, Agent, or Firm* — MacMillan, Sobanski & Todd, LLC (57) ABSTRACT

An articulating fusible support cage comprises a first support member having a first and second end and a second support member having a first and second end. A first end cap is pivotally connected to the first and second support members at the first ends. The first end cap supports a jackscrew for rotation. A second end cap is pivotally connected to the first and second support members at the second ends opposite the first ends. The second end cap has a threaded sleeve configured to engage a portion of the jackscrew. Rotation of the jackscrew into the threaded sleeve causes the first and second support members to extend outwardly from a collapsed condition to a deployed condition.

9 Claims, 7 Drawing Sheets

(52) U.S. Cl.
CPC ............... *A61F 2002/30579* (2013.01); *A61F 2002/30624* (2013.01); *A61F 2220/0025* (2013.01)

(58) Field of Classification Search
USPC ........... 623/17.15, 17.16, 17.11; 606/90, 105
See application file for complete search history.

(56) References Cited

U.S. PATENT DOCUMENTS

| | | | |
|---|---|---|---|
| 5,665,122 A | 9/1997 | Kambin | |
| 5,865,848 A * | 2/1999 | Baker | 623/17.15 |
| 6,039,761 A * | 3/2000 | Li et al. | 623/17.16 |
| 6,193,757 B1 * | 2/2001 | Foley et al. | 623/17.16 |
| 6,409,766 B1 | 6/2002 | Brett | |
| 6,443,989 B1 | 9/2002 | Jackson | |
| 6,454,807 B1 | 9/2002 | Jackson | |
| 6,464,727 B1 | 10/2002 | Sharkey et al. | |
| 6,478,823 B1 | 11/2002 | Michelson | |
| 6,572,653 B1 | 6/2003 | Simonson | |
| 6,582,451 B1 * | 6/2003 | Marucci et al. | 606/207 |
| 6,685,742 B1 | 2/2004 | Jackson | |
| 6,695,882 B2 | 2/2004 | Bianchi et al. | |
| 6,719,794 B2 | 4/2004 | Gerber et al. | |
| 6,719,795 B1 | 4/2004 | Cornwell et al. | |
| 6,743,257 B2 | 6/2004 | Castro | |
| 6,821,298 B1 | 11/2004 | Jackson | |
| 6,835,206 B2 | 12/2004 | Jackson | |
| 6,887,273 B2 | 5/2005 | Ralph et al. | |
| 6,893,464 B2 | 5/2005 | Kiester | |
| 6,974,480 B2 | 12/2005 | Messerli et al. | |
| 7,052,515 B2 | 5/2006 | Simonson | |
| 7,074,239 B1 | 7/2006 | Cornwall et al. | |
| 7,094,257 B2 | 8/2006 | Mujwid et al. | |
| 7,097,647 B2 * | 8/2006 | Segler | 606/90 |
| 7,223,291 B2 | 5/2007 | Errico et al. | |
| 7,223,292 B2 | 5/2007 | Messerli et al. | |
| 7,261,739 B2 | 8/2007 | Ralph et al. | |
| 7,270,680 B2 | 9/2007 | Ralph et al. | |
| 7,273,498 B2 | 9/2007 | Bianchi et al. | |
| D553,744 S | 10/2007 | Park | |
| 7,300,465 B2 | 11/2007 | Paul et al. | |
| 7,314,487 B2 | 1/2008 | Ralph et al. | |
| 7,329,283 B2 | 2/2008 | Estes et al. | |
| 7,347,873 B2 | 3/2008 | Paul et al. | |
| 7,901,409 B2 * | 3/2011 | Canaveral et al. | 606/86 R |
| 8,628,576 B2 * | 1/2014 | Triplett | A61F 2/4465 623/17.11 |
| 2003/0220650 A1 * | 11/2003 | Major et al. | 606/90 |
| 2003/0236520 A1 | 12/2003 | Lim et al. | |
| 2004/0087994 A1 * | 5/2004 | Suddaby | 606/190 |
| 2004/0102847 A1 | 5/2004 | Sato et al. | |
| 2005/0060035 A1 | 3/2005 | Errico et al. | |
| 2005/0070911 A1 * | 3/2005 | Carrison et al. | 606/90 |
| 2005/0273135 A1 * | 12/2005 | Chanduszko et al. | 606/213 |
| 2006/0142859 A1 | 6/2006 | McLuen | |
| 2006/0253423 A1 * | 11/2006 | McLane et al. | 707/2 |
| 2007/0093899 A1 | 4/2007 | Dutoit et al. | |
| 2007/0260314 A1 | 11/2007 | Biyani | |
| 2008/0046085 A1 * | 2/2008 | Zucherman et al. | 623/17.16 |
| 2008/0114367 A1 * | 5/2008 | Meyer | 606/90 |
| 2008/0243255 A1 * | 10/2008 | Butler et al. | 623/17.16 |
| 2009/0076607 A1 * | 3/2009 | Aalsma et al. | 623/17.16 |
| 2012/0071977 A1 * | 3/2012 | Oglaza et al. | 623/17.11 |

FOREIGN PATENT DOCUMENTS

| | | | | |
|---|---|---|---|---|
| WO | 2007111979 A2 | 10/2007 | | |
| WO | WO20101033444 | * | 9/2010 | A61B 17/7065 |

OTHER PUBLICATIONS

Supplementary European Search Report, Application No. EP 10751488.7 dated Jun. 5, 2013.

* cited by examiner

MINIMALLY INVASIVE COLLAPSIBLE CAGE

CROSS-REFERENCE TO RELATED APPLICATIONS AND STATEMENT REGARDING FEDERALLY SPONSORED RESEARCH

The invention claims the benefit of the U.S. Provisional Patent Application Ser. No. 61/160,051, filed Mar. 13, 2009, the disclosure of which is incorporated herein by reference in its entirety. This invention was made with no U.S. Government support and the U.S. Government has no rights in this invention.

BACKGROUND OF THE INVENTION

There is no admission that the background art disclosed in this section legally constitutes prior art.

The human spine includes thirty-three vertebrae. The vertebrae are vertically separated and cushioned from each other by fibro-cartilaginous structures commonly referred to as "discs." The discs can become damaged or diseased thereby causing a deterioration of the discs. Deterioration of discs can lead to severe back problems.

One approach to dealing with damaged, diseased discs is to remove and replace the affected discs with artificial discs. Another approach to dealing with damaged diseased discs is to remove and replace the affected discs with fusion cages. Over time, the adjacent vertebrae fuse together over the fusion cages and provide support to the spinal column.

What is needed is a fusion cage that provides improved support to the adjacent vertebrae and which can be implanted through a single small incision. The invention provides an improved fusion cage.

SUMMARY OF THE INVENTION

In a first aspect, there is provided herein an articulating support cage that comprises a first support member having a first and second end and a second support member having a first and second end. A first end cap is pivotally connected to the first and second support members at the first ends. The first end cap supports a jackscrew for rotation. A second end cap is pivotally connected to the first and second support members at the second ends opposite the first ends. The second end cap has a threaded sleeve configured to engage a portion of the jackscrew. Rotation of the jackscrew into the threaded sleeve causes the first and second support members to extend outwardly from a collapsed condition to a deployed condition.

In another aspect, there is provided herein an articulating support cage for disc replacement within a spinal column that includes a first end cap having a jackscrew and a pair of hinge elements. The jackscrew is configured for rotational movement relative to the first end cap and is axially fixed within the first end cap. The jackscrew has a threaded section extending from the first end cap. A second end cap has a threaded sleeve and a pair of hinge elements. The threaded sleeve is configured to engage the threaded section of the jackscrew such that rotation of the jackscrew causes the first end cap to move toward the second end cap to a deployed condition. A pair of first leg segments has pivot ears at one end and are pivotally connected to the first end cap hinge element at the other end. A pair of second leg segments being pivotally connected to the first leg segment pivot ears and pivotally connected to the second end cap, the first leg segment pivot ears causing the first and second leg segments to be outwardly displaced relative to the first and second end cap hinge elements when the support cage is in a collapsed condition.

In another aspect, there is provided herein an articulating support cage where the first and second support members and the first and second end caps cooperate to define a profile having a parallel upper and lower surfaces. Alternatively, the profile may be configured as tapered upper and lower surfaces. The upper and lower surfaces may include an anchoring profile that is one of a plurality of teeth or a groove.

In another aspect, there is provided herein a method of implanting an articulating support cage including the steps of removing a disc from between adjacent vertebrae thereby creating a gap, providing an articulating support cage having first and second support members pivotally connected to first and second end caps. The first end cap supports a jackscrew for relative rotational movement and a fixed relative axial position. A threaded portion of the jackscrew engages a threaded sleeve extending from the second end cap. Rotation of the jackscrew causes the first and second end caps to move together and further causes the first and second support members to expand outwardly. The articulating support cage is moved to a collapsed position where the first and second end caps are positioned apart and the first and second support members are moved next to the threaded sleeve and jackscrew. A disc, or a portion of a disc, between two vertebrae is removed forming a gap. The collapsed support cage is inserted into the gap through a small incision. As the support cage is inserted, the jackscrew is rotated to begin expanding the support members to a deployed position.

Other systems, methods, features, and advantages of the invention will be or will become apparent to one with skill in the art upon examination of the following drawings and detailed description. It is intended that all such additional systems, methods, features, and advantages be included within this description, be within the scope of the invention, and be protected by the accompanying claims.

BRIEF DESCRIPTION OF THE DRAWINGS

The following drawings may contain hidden features or elements shown in dotted lines and may include phantom views of various components or elements shown in dashed-dotted lines.

DETAILED DESCRIPTION OF THE PREFERRED EMBODIMENT(S)

Figure 1:
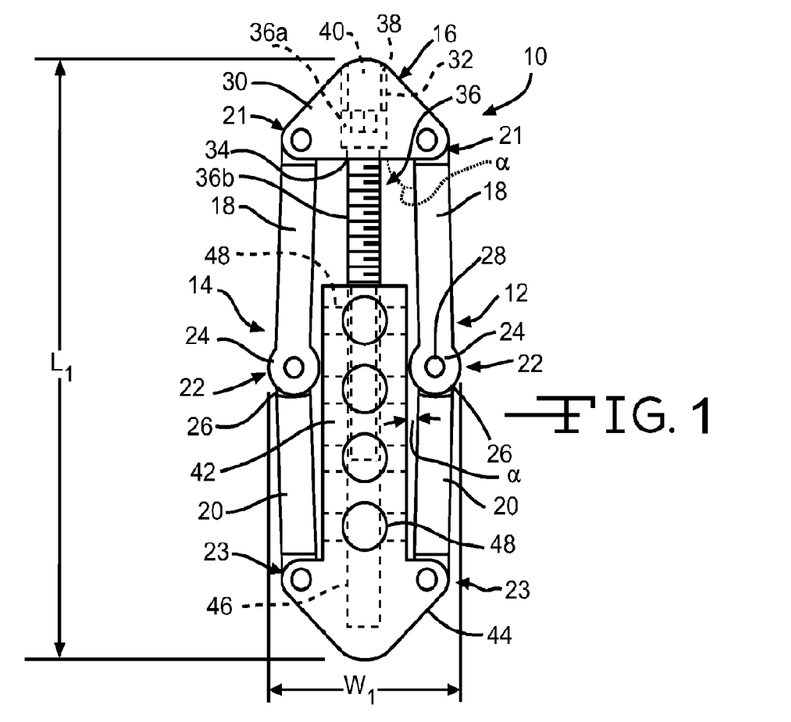
FIG. 1 is a plan elevational schematic view of an embodiment of an articulating fusible support cage, illustrated in a collapsed state.
Figure 2A:
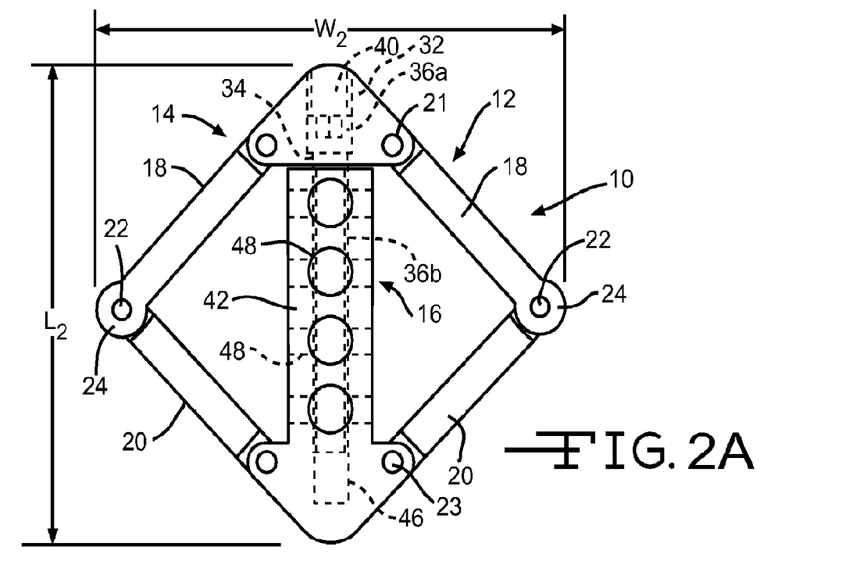
FIG. 2A is a plan elevational schematic view of an articulating fusible support cage, illustrated in a deployed state.
Figure 3:
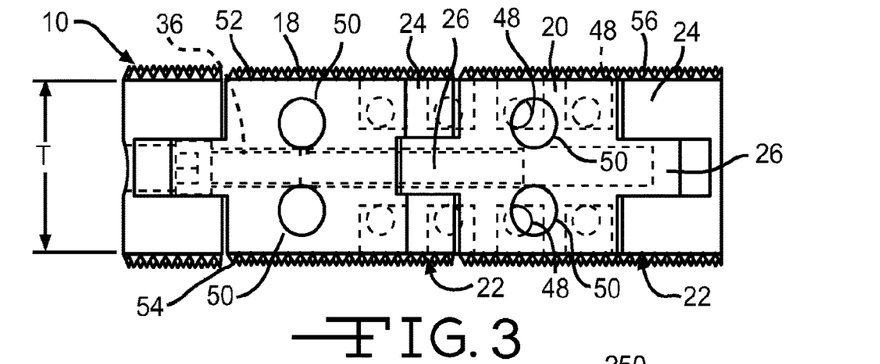
FIG. 3 is a side elevational schematic view of another embodiment of an articulating fusible support cage.

Referring now to the drawings, there is illustrated in FIG. 1 an embodiment of an articulating fusible support cage, shown generally at 10, in a collapsed or unexpanded state, ready for deployment. FIG. 2A shows the support cage 10 expanded to a deployed state. The articulating fusible support cage 10 includes a plurality of articulating support members, shown as first and second support members 12 and 14, and an actuator section, shown generally at 16. The first and second support members 12 and 14 each include a first leg segment 18 that is pivotally connected to a second leg segment 20 by way of a hinge element 22. The hinge element 22 may be any structure that permits one leg segment to pivot relative to the adjacent leg segment. As shown in FIG. 3, the hinge element 22 includes a pivot ear 24, shown on one end of the first leg segment 18, and a pivot tongue 26, shown on a mating end of the second leg segment 20. Referring again to FIG. 1, the pivot ear 24 is connected for rotation relative to the pivot tongue 26 by a hinge pin 28.

Though shown as having two leg segments 18 and 20, the first and second support members 12 and 14 may have more than two leg segments. Where more than two leg segments are employed, a resilient member (not shown) may be used to urge the leg segments away from the actuator section 16 during deployment. Alternatively, the hinge elements may include cooperating gear teeth (not shown) on adjacent pivot points that articulate the leg segments away from the actuator section 16.

The actuator section 16 includes a first end cap 30 and a second end cap 44 that are connected by a jackscrew 36 and an internally threaded sleeve 42. It is to be understood that, in certain embodiments, the second end cap 44 and the threaded sleeve 40 can be formed as an integral unit, as schematically illustrated herein. In other embodiments, the second end cap 44 and the threaded sleeve 42 can be distinct elements.

The first end cap 30 is pivotally connected to the first leg segments 18 of the first and second support members 12 and 14 by opposing hinge elements 21. In the illustrated embodiment of FIGS. 1 and 2A, the first end cap 30 includes a counterbored aperture 32 having a retaining lip 34. The counterbored aperture 32 is configured to receive the jackscrew 36 which has a torque-transmitting head 36a and a threaded section 36b. In the illustrated embodiment, the counterbored aperture 32 is sized to permit the jackscrew head 36a to be freely inserted and rotate therein. The retaining lip 34 retains the jackscrew head 36a in one direction within the aperture 32. In certain embodiments, a retaining sleeve 38 having an access hole 40 may be press fit or otherwise secured within the aperture 32 to trap the jackscrew head 36a. Thus, the jackscrew 36 is permitted to rotate relative to the first end cap 30 yet is restrained axially within the first end cap 30. The access hole 40 is sized to permit a key (not shown), such as an allen wrench or a screw driver, to engage the jackscrew head 36a and rotate the jackscrew 36. Alternatively, the jackscrew head 36a may be retained by a pin (not shown) that extends across a portion of the head 36a. In another embodiment, the retaining lip 34 may be a flange that is roll-formed onto the jackscrew head 36a.

The jackscrew threaded section 36b extends past the retaining lip 34 and engages the threaded sleeve 42 that extends from the second end cap 44. The second end cap 44 is pivotally connected to the second leg segments 20 of the first and second support members 12 and 14 by opposing hinge elements 23. The threaded sleeve 42 includes an internally threaded bore 46 configured to receive the jackscrew threaded section 36b. The threaded sleeve 42 also may include a plurality of locking apertures 48 formed either on the surface or extending through the sleeve 42. The locking apertures 48 of the threaded sleeve 42 may be infused with a filler material configured as a bone growth medium, such as bone chips, in order to cause the vertebrae to fuse to the cage 100. Alternatively, other filler materials may be used in place of a bone growth medium.

Referring now to FIG. 2A, the support cage 10 is shown in a deployed condition where the first and second support members 12 and 14 are extended outwardly from the actuator section 16. As the jackscrew 36 is rotated, the first end cap 30 is drawn toward the threaded sleeve 42 by the head 36a pressing against the retaining lip 34. In the illustrated embodiment shown in FIG. 1, when the support cage 10 is in a collapsed state, the pivot ears 24 of the first leg segment 18 are shaped to orient the first and second leg segments 18 and 20 at a slight outwardly extending angle, α, with respect to the actuator section 16. The outwardly extending angle, α, orients the hinge elements 22 of the first and second leg segments 18 and 20 beyond a plane defined by the hinge elements 21 and 23 that connect the first and second end caps 30 and 44 to the first and second leg segments 18 and 20. Thus, in operation as the jackscrew 36 is rotated, the leg segments 18 and 20 are forced away from the actuator section 16 and into the deployed condition. Thus, the opposing first and second support members 12 and 14 of the articulating fusible support cage 10 are configured to spread out across a disc space between adjacent vertebrae rather than being expanded against the vertebrae, as further explained herein.

As shown in FIG. 1, the articulating fusible support cage 10 has a collapsed length L1 and a collapsed width W1. In one example, the collapsed length L1 may be approximately 25 mm and the collapsed width W1 may be approximately 10 mm. It should be understood that the length and width may be any suitable dimensions. As the first and second support members 12 and 14 are extended outwardly, as shown in FIG. 2A, they may be moved out to a deployed length L2 and a deployed width W2, or any distance between the collapsed and deployed dimensions. In one embodiment, the deployed length L2 may be approximately 15 mm and the deployed width W2 may be approximately 25 mm.

Figure 2B:
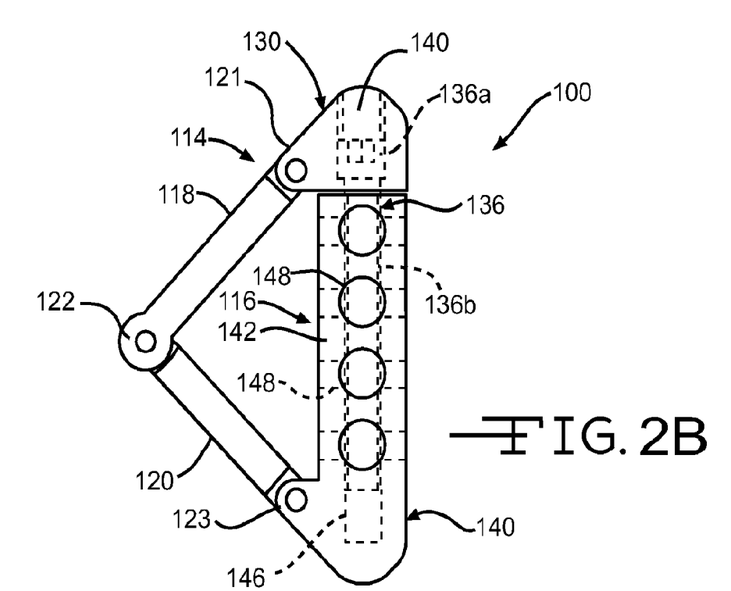
FIG. 2B is a plan elevational schematic view of another embodiment of an articulating fusible support cage illustrated in a deployed state.

Referring now to FIG. 2B, there is illustrated another embodiment of an articulating fusible support cage, shown generally at 100. The support cage 100 includes a single sided support member 114 and an actuator section 116. The support member 114 includes first and second leg segments 118 and 120, respectively. As described above, the support member 114 may have more than the first and second leg segments 118 and 120 shown in FIG. 2B. The first and second leg segments 118 and 120 are pivotally connected by a hinge element 122. The first leg segment 118 is also pivotally connected to a first end cap 130 by opposing hinge element 121. The second leg segment 120 is connected to a second end cap 144 by opposing hinge element 123. The first end cap 130 includes a jackscrew 136 having a torque-transmitting head 136a and a jackscrew threaded section 136b, and can be configured in a similar manner to the jackscrew 36, described above. The second end cap 144 includes a threaded sleeve 142 that engages the jackscrew 136. The threaded sleeve 142 can include locking apertures 148 that may be infused with a material configured as a bone growth medium such as bone chips, in order to cause the vertebrae to fuse to the cage 100. As the jackscrew 136 is rotated, the first end cap 130 is drawn toward the second end cap 144 in a similar manner as described above. The first and second leg segments 118 and 120 pivot at the hinge elements 122 and extend outwardly.

Figure 11:
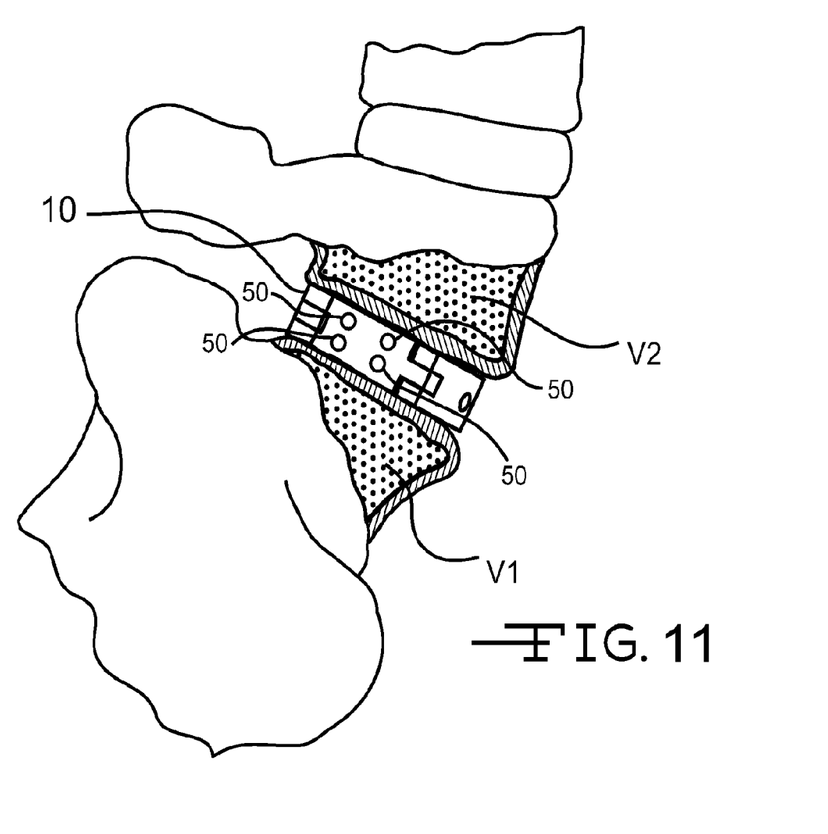
FIG. 11 is a side elevational schematic view of a portion of a human spinal column having an articulating fusible support cage inserted and deployed between two adjacent vertebrae, partially in cross section.

Referring now to the embodiment shown in FIG. 3, the first and second leg segments 18 and 20 include locking apertures 50, shown as being generally round in shape. The locking apertures 50 and the locking apertures 48 are provided as anchor points for subsequent bone growth to penetrate. When the articulating fusible support cage 10 is moved to the deployed condition, shown in FIG. 2, spaces that are formed between the first and second support members 12 and 14 and the actuator section 16 also provide locations for bone growth between adjacent vertebrae. Additionally, bone chips may be injected, infused or otherwise provided in the spaces to aid in bone fusion between the adjacent vertebrae. Alternatively, another medium, such as a polymer, epoxy or material simulating the mechanical properties of a spinal disc may be provided around the articulating fusible support cage 10 and through the locking apertures 48 and/or 50. In certain embodiments, the locking apertures 50 may also provide passageways for anchoring screws (not shown) that anchor the cage 10 to the upper and lower vertebrae V1 and V2, as shown in FIG. 11.

Figure 4:
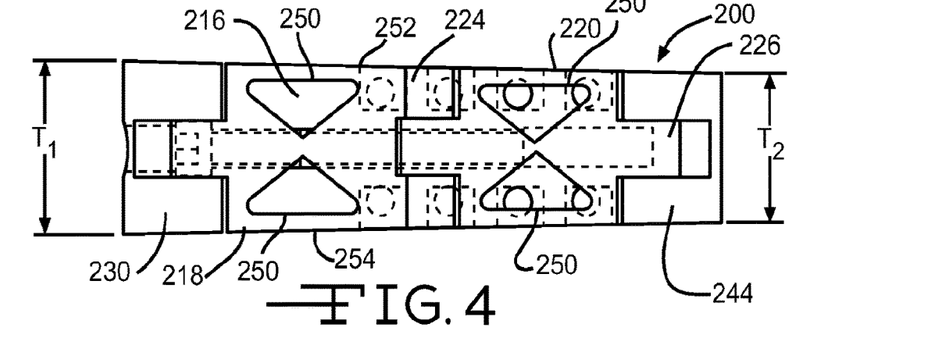
FIG. 4 is a side elevational schematic view of another embodiment of an articulating fusible support cage.

Referring now to FIGS. 3 and 4, there are illustrated two embodiments of articulating fusible support cages 10 and 200 having different profile configurations. The articulating fusible support cage 10 includes upper and lower surfaces 52 and 54 that are generally parallel to each other. Thus, the articulating fusible support cage 10 has a generally constant thickness, T. In certain embodiments, at least the upper and lower surfaces 52 and 54 can have a plurality of teeth 56 disposed across the upper and lower surfaces 52 and 54 of the support cage 10. The teeth 56 may be configured as any gripping surface that generally prevents or limits movement of the cage 10 relative to adjacent vertebra.

The articulating fusible support cage 200, shown in FIG. 4, is substantially similar to the articulating fusible support cage 10. The articulating fusible support cage 200 includes an actuator section 216. The support cage 200 also includes a first leg segment 218 having pivot ears 224 that pivotally connect to a second leg segment 220. The first leg segment 218 is also pivotally connected to a first end cap 230. The second leg segment 220 includes a pivot tongue 226 that is pivotally connected to a second end cap 244. The articulating fusible support cage 200 has a tapered profile from a first end having a thickness of T1 to a second end having a thickness of T2, where T1 is greater than T2. In the illustrated embodiment, the tapered profile extends over the length of the cage 200 from the first end cap 230 to the second end cap 244 and across an upper surface 252 and a lower surface 254. It will be appreciated that the tapered profile may be oriented in other planes so that when the articulating fusible support cage 200 is in the deployed state, the tapered profile is similar to FIG. 4. For example, the profile may extend from the first leg segment 218 to the second leg segment 220 that is on the opposite side of the actuator section 216. In the illustrated embodiments of the articulating fusible support cages 10 and 200, the upper surfaces 52 and 252 and lower surfaces 54 and 254 are generally flat and smooth.

Figure 5:
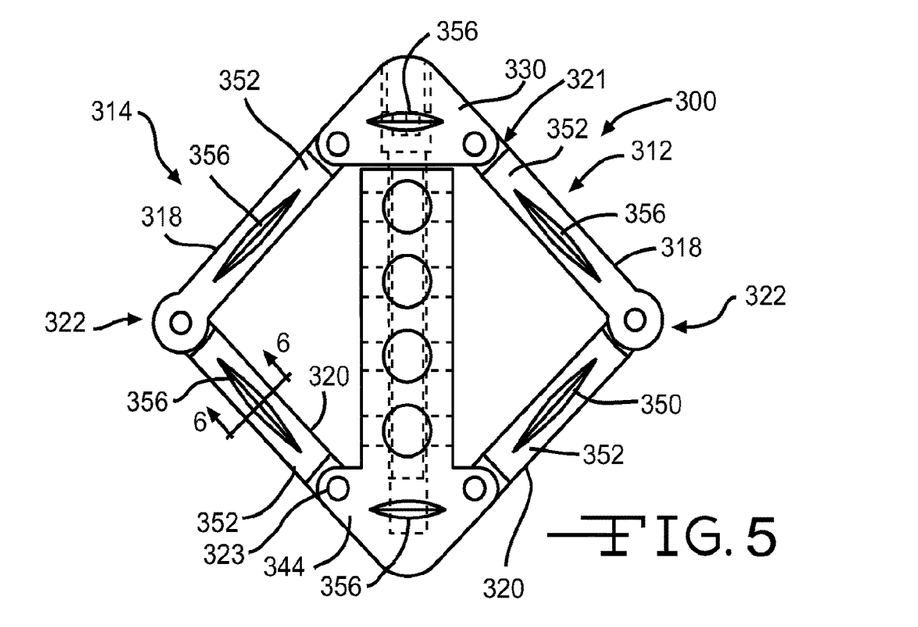
FIG. 5 is a plan elevational schematic view of another embodiment of an articulating fusible support cage, illustrated in a deployed state.
Figure 6A:
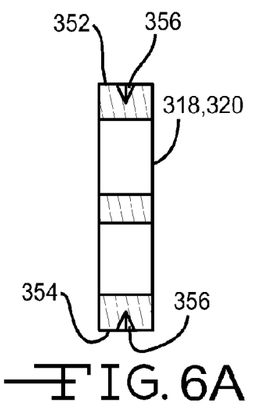
FIG. 6A is an end view, in cross section, of a portion of the articulating fusible support cage of FIG. 5, shown partially in cross section.

Referring now to FIG. 5, there is illustrated another embodiment of an articulating fusible support cage, shown generally at 300. The articulating fusible support cage 300 includes first and second support members 312 and 314 that are pivotally connected to a first end cap 330 and a second end cap 344 by opposing hinge elements 321 and 323, respectively. The first and second support members 312 and 314 each include at least two pivotally connected leg segments, illustrated as first and second leg segments 318 and 320 that are each connected by opposing hinge elements 322. The first and second leg segments 318 and 320 include an anchoring profile, shown as a groove 356 in FIGS. 5, 6A, and 6B, formed on a portion of at least an upper surface 352. The groove 356 is illustrated as having a generally triangular cross section and a generally diamond plan view shape. However, the groove 356 may be any shape, either recessed into or extending from the upper surface 352. As shown in FIG. 6A, the groove 356 may be formed on both the upper surface 352 and a lower surface 354, if desired. The groove 356, when configured as an embedded groove, may include bone chips, adhesive, or other material to fix the support cage 300 to adjacent vertebrae. When configured as an extending diamond shaped anchoring profile, the groove 356 may be embedded into the adjacent vertebrae to prevent movement of the support cage 300 in order to promote bone growth and fusion of the cage to the vertebrae.

Figures 6B, 6C, 6D:
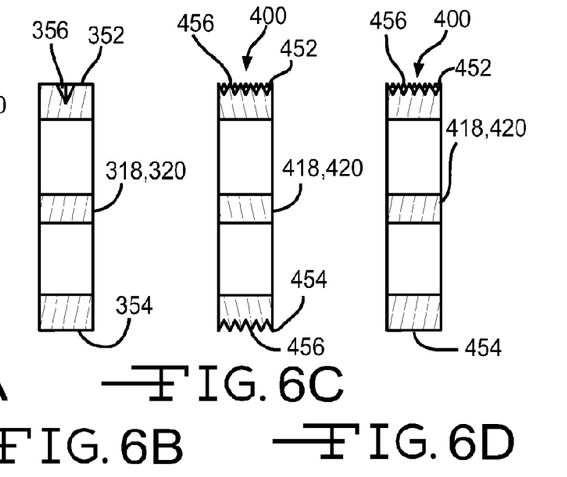
FIG. 6B is an end view, in cross section, of an other embodiment of a portion of an articulating fusible support cage, shown partially in cross section.
FIG. 6C is an end view, in cross section, of an other embodiment of a portion of an articulating fusible support cage, shown partially in cross section.
FIG. 6D is an end view, in cross section, of an other embodiment of a portion of an articulating fusible support cage, shown partially in cross section.

Referring now to FIGS. 6C and 6D, there are illustrated two variations of another embodiment of a portion of an articulating fusible support cage 400. An embodiment of a first leg segment 418, shown in FIG. 6C, includes an upper surface 452 having an anchoring profile comprising a plurality of extending projections 456. The projections 456 may be teeth, formed in straight or staggered rows or a knurled surface that inhibits relative movement between the support cage 400 and adjacent vertebrae. The anchoring profile is also applicable to a second leg segment 420, or any other surface of the cages described herein. The profiles of FIGS. 6A-6D provide an engagement interface to fix the position of the various embodiments of the support cage relative to adjacent vertebrae. The anchoring profiles become embedded in the surfaces of the adjacent vertebrae which prevents movement and promotes bone growth around the cage.

Figure 7:
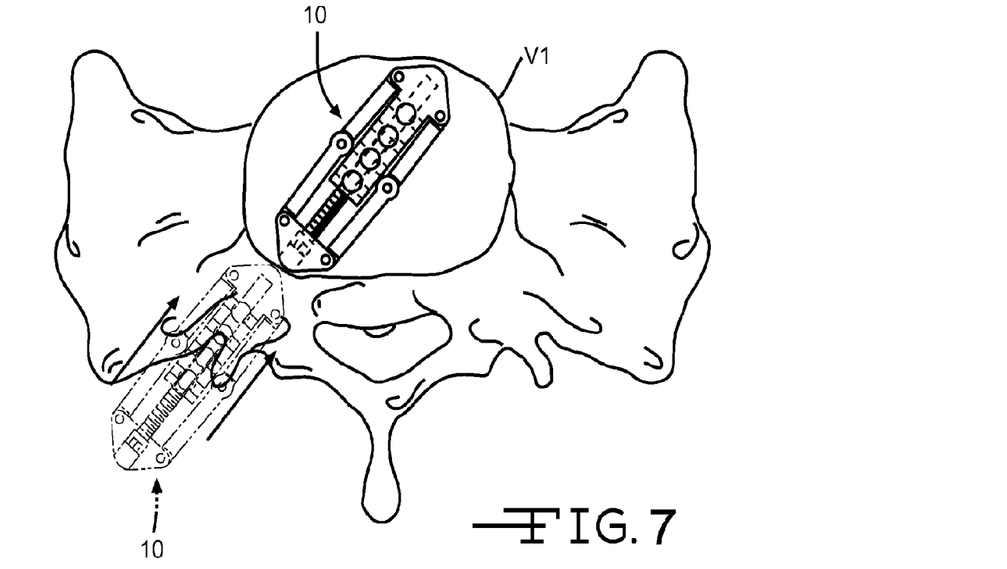
FIG. 7 is a plan elevational schematic view illustrating a method of inserting an articulating fusible support cage, first in an external position (in phantom) and then in an internal position.

Referring now to FIGS. 7-11, there is illustrated one embodiment of a method of implanting the support cage 10. Referring first to FIG. 11, the articulating fusible support cage 10 is shown as being inserted between adjacent vertebrae V1 and V2. As shown in FIGS. 7 and 11, the articulated fusible support cage 10 is inserted in a disc space S and over the surface of vertebra V1 in a collapsed condition as part of a minimally invasive surgical procedure to minimize incision size and speed patient recovery time. The support cage 10 may also be inserted between adjacent vertebrae from the posterior, lateral, or anterior side of the patient.

Figure 8:
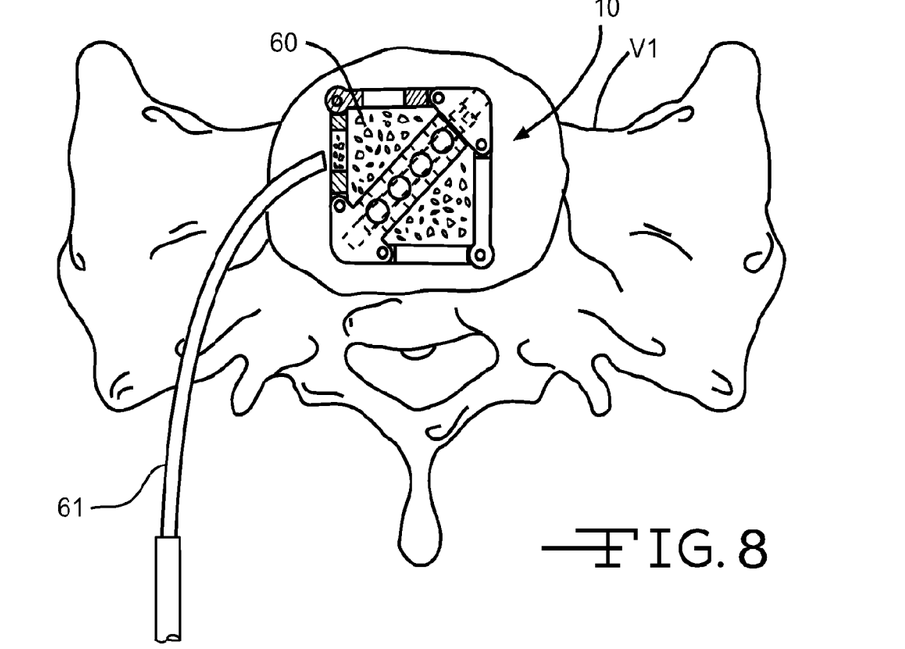
FIG. 8 is a plan elevational schematic view of an embodiment of a method of deploying an inserted articulating fusible support cage, shown partially in cross section.
Figure 9:
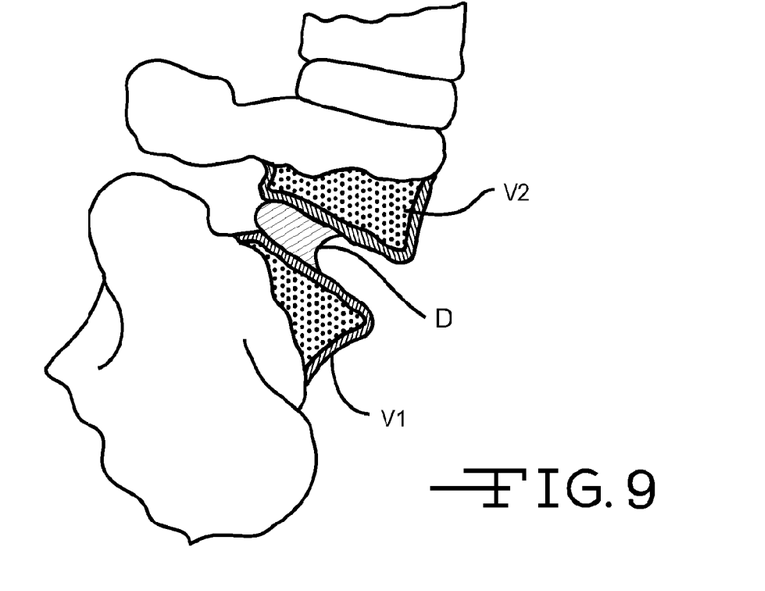
FIG. 9 is a side elevational schematic view of a portion of a human spinal column having a diseased disc, partially in cross section.
Figure 10:
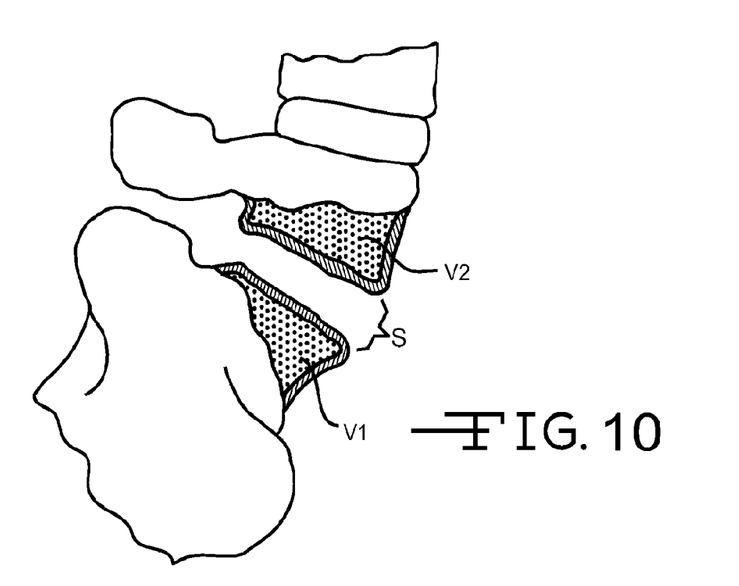
FIG. 10 is a side elevational schematic view of a portion of a human spinal column having a disc removed prior to insertion of an articulating fusible support cage, partially in cross section.

As shown in FIGS. 9 and 10, a diseased or damaged disc, D, or a portion of the disc, is removed from between the vertebrae. The configuration of a space, S, between adjacent vertebrae may suggest a choice of the constant thickness support cage 10 or the tapered profile support cage 200. The support cage 10, articulated to the collapsed condition, is inserted through an incision (not shown). During and/or after the hinge elements 22, located between the first and second leg segments 18 and 20, pass through the incision, the jackscrew 36 may be rotated to begin expanding the support cage 10. The support cage 10 may be expanded completely or partially depending upon the area requiring support. As shown in FIGS. 8 and 11, with the disc completely removed, the support cage 10 is expanded outwardly to the fully deployed position.

The support cage 10 is configured to be expanded and contracted by rotation of the jackscrew 36 as explained previously. Additionally, the support cage 10 is prevented from expanding or contracting without rotation of the jackscrew 36. This allows the final size of the support cage 10 to be fixed at any point between the fully collapsed and fully extended positions. Since the jackscrew 36 actively drives the first and second support members 12 and 14 outwardly, the movement of the support members 12 and 14 also tends to clear out surgical debris within the disc space S. Often, prior art support cages are inhibited from properly deploying because the surgical debris blocks a clear path of expansion.

Once the support cage 10 is deployed within the spinal column, the adjacent vertebrae V1 and V2 are brought into contact with the expanded first and second support members 12 and 14.

It is to be understood that the first and second end caps 30, 44 and the threaded sleeve 42 also are load bearing structures and support the compressive, shear and tensile loads imparted by the spine. Thus, the upper and lower support surfaces 52 and 54 can extend across the entire support cage 10. As shown in FIG. 8, the spaces defined by the expanded support cage 10 may be filled with bone chips 60 to aid in bone fusion between the adjacent vertebrae, using a suitable dispensing mechanism 61. Bone chips 60 may be injected, infused or otherwise provided in the spaces of the expanded support cage 10. Alternatively, another medium, such as a polymer, epoxy or material simulating the mechanical properties of a spinal disc may be provided around the articulating fusible support cage 10.

Figure 12A:
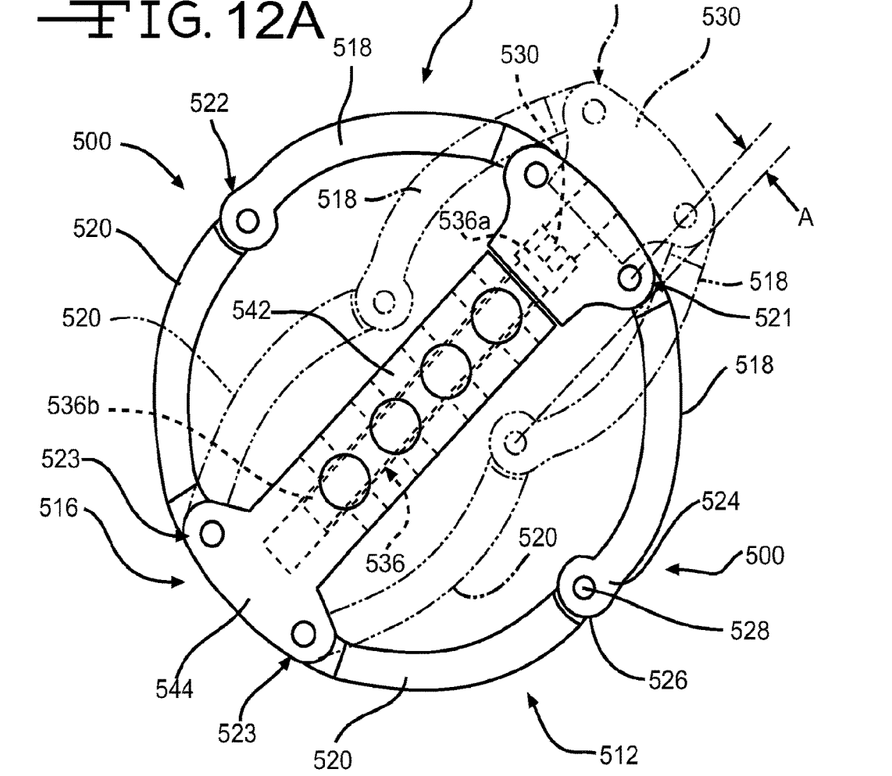
FIG. 12A is a plan elevational schematic view of another embodiment of an articulating fusible support cage, shown in a collapsed state (in phantom) and in an expanded state.

Referring now to FIG. 12A, there is illustrated another embodiment of an articulated fusion support cage, shown generally at 500. The support cage 500 includes a plurality of arcuately-shaped, articulating support members, shown as first and second support members 512 and 514, and an actuator section, shown generally at 516. In the illustrated embodiment, the arcuately-shaped first and second support members 512 and 514 provide a generally circular circumference to the support cage 500 when fully expanded.

The first and second support members 512 and 514 each include an arcuate first leg segment 518 that is pivotally connected to an arcuate second leg segment 520 by way of a hinge element 522. The hinge element 522 may be any structure that permits one leg segment to pivot relative to the adjacent component. In the illustrated embodiment, the hinge element 522 includes a pivot ear 524, shown on one end of the first leg segment 518, and a pivot tongue 526, shown on a mating end of the second leg segment 520, similar to the support cage 10 described above. The pivot ear 524 is connected for rotation relative to the pivot tongue 526 by a hinge pin 528.

The actuator section 516 includes a first end cap 530 that is pivotally connected to each of the first leg segments 518 of the first and second support members 512 and 514 by opposing hinge elements 521. The first end cap 530 supports a jackscrew 536, similar to jackscrew 36 described above, having a head 536a and a threaded section 536b. The jackscrew threaded section 536b engages a threaded sleeve 542 that extends from a second end cap 544 as part of the articulator section 516. The second end cap 544 is pivotally connected to each of the second leg segments 520 of the first and second support members 512 and 514 by opposing hinge elements 523.

When the arcuate first and second leg segments 518 and 520 are in the collapsed position, shown in phantom, the hinge elements 522 connecting the first leg segments 518 to the second leg segments 520 are offset outwardly from a plane of the hinge elements 522 of the first and second end caps 530 and 544. The offset "A" permits the leg segments 518 and 520 to expand outwardly as the jackscrew 536 is rotated and the first and second end caps 530 and 544 are drawn together.

Figure 12B:
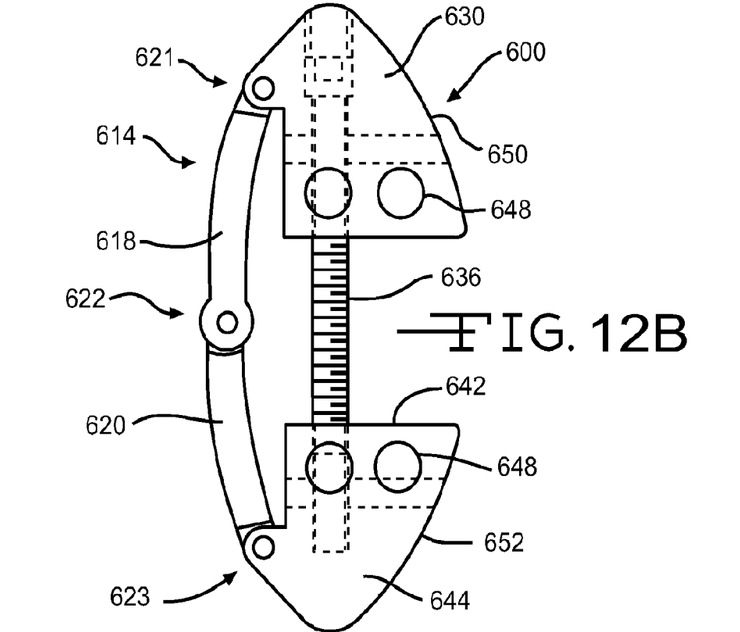
FIG. 12B is a plan elevational schematic view of another embodiment of an articulating fusible support cage, illustrated in a collapsed state.

Referring now to FIG. 12B, there is illustrated another embodiment of an articulating fusible support cage, shown generally at 600. The support cage 600 is a single sided support cage, similar to the support cage 100, shown in FIG. 2B. The support cage 600 includes a single sided support member 614. The support member 614 includes arcuately-shaped first and second leg segments 618 and 620, respectively. As described above, the support member 614 may have more than the first and second leg segments 618 and 620 shown in FIG. 12B. The first and second leg segments 618 and 620 are pivotally connected by a hinge element 622. The first leg segment 618 is also pivotally connected to a first end cap 630 by hinge element 621. The first end cap 630 includes a profile 650 that is generally arcuate in shape. The first end cap 630 having the profile 650 creates a larger surface area to support the vertebrae V1 and V2. Likewise, the second leg segment 620 is connected to a second end cap 644 by hinge element 623. Similarly, the second end cap 644 includes a profile 652 that is generally arcuately shaped to create a larger support area for adjacent vertebrae.

The first end cap 630 includes a jackscrew 636, configured in a similar manner to the jackscrew 136, described above. The second end cap 644 includes a threaded sleeve 642 that engages the jackscrew 636. The threaded sleeve 642 (and/or the first end cap 630) can include locking apertures 648 that may be infused with a material such as bone chips, in order to cause the vertebrae to fuse to the cage 600. As the jackscrew 636 is rotated, the first end cap 630 is drawn toward the second end cap 644 in a similar manner as described above. The first and second leg segments 118 and 120 pivot about the hinge elements 621, 622, and 623 and extend outwardly. The support cage 600 provides a generally rounded triangular shape when moved to the deployed position.

Figure 13:
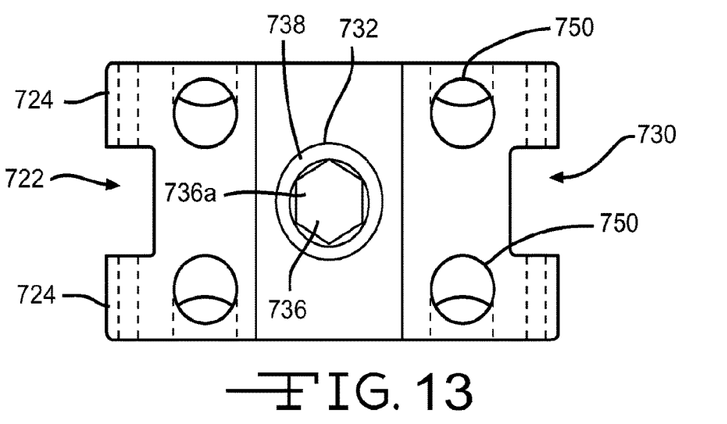
FIG. 13 is an elevational schematic view of an embodiment of a portion of an articulating fusible support cage having an anchoring structure.

Referring now to FIG. 13, there is illustrated an embodiment of a first end cap 730 that includes a pivot ear 724 portion of a hinge element 722 and a counterbored aperture 732. The counterbored aperture 732 holds a jackscrew 736, configured similarly to jackscrew 36. The jackscrew may be retained in the counterbored aperture 732 by a retaining sleeve 738 positioned against a jackscrew head 736*a*. The end cap 730 includes a plurality of anchoring apertures 750. In certain embodiments, the anchoring apertures 750 can be angled toward the adjacent vertebrae to accommodate anchoring screws (not shown). It should be understood that a second end cap (not shown) may be configured with similar anchoring apertures 750, may also be provided as part of any of the above described cage embodiments.

While the invention has been described with reference to particular embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiments disclosed herein contemplated for carrying out this invention, but that the invention will include all embodiments falling within the scope of the claims. Furthermore, elements of any embodiment described herein may be applied to another of the disclosed embodiments and is considered to be within the scope of the invention. The publication and other material used herein to illuminate the invention or provide additional details respecting the practice of the invention, are incorporated by reference herein.

What is claimed is:

1. A method comprising the steps of:
   (a) providing a support cage that includes:
      (1) a first leg segment connected to a first end cap;
      (2) a second leg segment connected to a second end cap;
      (3) a hinge pivotably connecting the first and second leg segments;
      (4) a jackscrew supported on the first end cap and having an externally threaded section; and
      (5) an internally threaded sleeve supported on the second end cap that cooperates with the externally threaded section of the jackscrew;
      wherein the first leg segment and the second leg segment define first and second vertebra-engaging surfaces that are separated by a distance;
   (b) inserting the support cage between first and second vertebrae such that the first vertebra-engaging surface engages the first vertebra and the second vertebra-engaging surface engages the second vertebra; and
   (c) rotating the jackscrew relative to the internally threaded sleeve so as to cause relative pivoting movement of the first and second leg segments from a collapsed condition, wherein the first end cap and the second end cap are positioned at a first distance from one another, to a deployed condition, wherein the first end cap and the second end cap are positioned at a second distance from one another that is less than the first distance, without changing the distance between the first and second vertebra-engaging surfaces.

2. The method defined in claim 1 wherein step (a) is performed by pivotably connecting the first leg segment to the first end cap and by pivotably connecting the second leg segment to the second end cap.

3. The method defined in claim 1 wherein step (a) is performed by providing parallel first and second vertebra-engaging surfaces.

4. The method defined in claim 1 wherein step (a) is performed by providing tapered first and second vertebra-engaging surfaces.

5. The method defined in claim 1 wherein step (a) is performed by providing first and second leg segments that are straight.

6. The method defined in claim 1 wherein step (a) is performed by providing first and second leg segments that are arcuate.

7. The method defined in claim 1 wherein step (a) is performed by providing the internally threaded sleeve with a plurality of locking apertures provided either on a surface thereof or extending therethrough.

8. The method defined in claim 1 wherein step (a) is performed by providing first and second vertebra-engaging surfaces having respective anchoring profiles provided thereon, and wherein step (b) is performed by engaging the anchoring profiles with the respective surfaces of the first and second vertebrae.

9. The method defined in claim 1 wherein:
   step (a)(1) is performed by providing a pair of first leg segments each connected to the first end cap;
   step (a)(2) is performed by providing a pair of second leg segment each connected to the second end cap; and
   step (a)(3) is performed by providing a pair of hinges pivotably connecting respective pairs of the first and second leg segments.

\* \* \* \* \*